United States Patent [19]

Baligadoo

[11] Patent Number: 5,455,269
[45] Date of Patent: Oct. 3, 1995

[54] SYNERGISTIC COMPOSITIONS OF AMIODARONE AND BETA BLOCKERS

[76] Inventor: Soorianarain Baligadoo, Center of Research Medicales, SSR, Univerisity de Maurice, Moka, Mauritius

[21] Appl. No.: 134,526

[22] Filed: Oct. 8, 1993

Related U.S. Application Data

[60] Continuation-in-part of Ser. No. 919,279, Jul. 27, 1992, Pat. No. 5,252,600, which is a division of Ser. No. 401,869, Mar. 6, 1989, Pat. No. 5,175,187.

[51] Int. Cl.$^6$ .......................... A61K 31/36; A61K 31/165
[52] U.S. Cl. ............................................ 514/464; 514/620
[58] Field of Search ..................................... 514/464, 620

OTHER PUBLICATIONS

The Merck Index, Eleventh Edition, 1989. pp. 79 and 136.

*Primary Examiner*—Zohreh Fay
*Attorney, Agent, or Firm*—Omri M. Behr; Matthew J. McDonald

[57] ABSTRACT

There are disclosed pharmaceutical preparations and methods for the use thereof which have a cardioprotective action useful in coronary insufficiency, in the prevention of the constitution of an infarction or of sudden death. It consists in the utilization of amiodarone and a beta-blocker at certain diodes and in certain ratios whereby the gravity of life of the patient is enhanced.

12 Claims, No Drawings

SYNERGISTIC COMPOSITIONS OF AMIODARONE AND BETA BLOCKERS

RELATED APPLICATIONS

This application is a continuation in part of application Ser. No. 919279, filed Jul. 27, 1992, now U.S. Pat. No. 5,252,600, which in turn is a divisional application of then application Ser. No. 401869, filed Mar. 6, 1989, now U.S. Pat. No. 5,175,187.

FIELD OF THE INVENTION

There are disclosed pharmaceutical preparations and methods for the use thereof which have a cardioprotective action useful in coronary insufficiency, in the prevention of the constitution of an infarction or of sudden death. These methods comprise the utilization of amiodarone, a nitrate derivative and a beta-blocker.

BACKGROUND OF THE INVENTION

In coronary insufficiency, one observes a high frequency of sudden death particularly in acute coronary insufficiency which may culminate in the occurrence of myocardial infarction. Some cases of sudden death are related to arrhythmias consecutive to coronary insufficiency Itself. It would be desirable to contemporaneously decrease the consumption of oxygen, increase the myocardial irrigation and also exercise a preventive effect against arrhythmias.

It has been observed that coronary thrombosis induces a phenomenon called stunned myocardial syndrome consecutive to the prolonged ischaemia of the heart. This phenomenon prevents the obtention of optimal benefits following reperfusion.

SUMMARY OF THE INVENTION

The utilization of a nitrate compound has previously been found desirable in the first hours of an infarction. Applicant herein has demonstrated the usefulness of a nitrate free system in the treatment of acute coronary insufficiency, infarction and in the treatment of the ischaemia present in the border zone of an infarct and in the area threatened by infarction.

This work demonstrated the existence of sub-groups of patients where the undesirable effects of the administration of a nitrate derivative were relatively important. Hence, it would be desirable to administer a composition which cancels the secondary effects, intensifies the anti-ischemic effect and allows a more prolonged anti-ischemic effect with a clinically detectible synergy.

There is provided a method of obtaining cardioprotective action for a patient suffering from coronary insufficiency and thereby reducing the probability of incidence of myocardial infarction in such a patient which comprises administering to such patient a cardioprotectively sufficient amount of protective agents comprising amiodarone in conjunction with at least one member of the group consisting of a beta blocker. Suitably, the beta blocker is selected from the group consisting of acebutolol, metoprolol and atenolol. The recitation of beta blockers is not intended as limiting or critical.

The protective agents are administered separately or in associated form by at least one of the routes of administration selected from the group of methods consisting essentially of oral, sublingual, intravenous, subcutaneous, and inhalation administrative routes.

In one mode, the protective agents are administered within the first 30 minutes after onset of apparent cardiac insufficiency and, suitably, the administration is repeated at least once at intervals of between 30 and 60 minutes after the first administration.

The above identified agents may comprise amiodarone and a beta blocker. Suitably, the ratio by weight of amiodarone to beta blocker is 100 to between 8 and 25 and the total administered dosage is between about 2 and about 30 mg per kg bodyweight per day.

It is within the contemplation of the present invention that the compositions disclosed herein may be utilized with fibrinolytic agents such as streptokinase, urokinase, eminase, RTPA and the like.

CLINICAL STUDIES

Clinical experiments were performed to determine the efficacy of certain cardioprotective agents. In the first series of experiments studies were carried out on 50 consecutive patients with an acute myocardial infarction, to observe the effects of the administration of intravenous isosorbide dinitrate at a dose varying from 2,5 to 7,5 mg per hour. The effect of intravenous amiodarone only administered during 24 hours was also studied in 50 consecutive patients with a myocardial infarction at a dose of 10 mg/kg/24 hrs.

The observation by the applicant of synergy occurring clearly with doses of amiodarone, that may be considered to be high, together with nitrates, prompted further studies on synergy between amiodarone and other drugs with a view of reducing the size of the initial bolus dose. The applicant performed studies with a number of drugs including dypindamole, calcium blockers and beta blockers and noted clear synergy in bolus doses only between amiodarone and a beta-blocker. It was clearly observed in cases of severe angina with repeated frequent episodes of severe angina, clinically and electrically well-defined that the episodes could be prevented by the administration of bolus doses of Amiodarone 25 mg and propanolol 1 mg.

However the association of amiodarone and a beta-blocker is contra-indicated in French text books and in the French guidelines for doctors and is therefore not suggested by the state of the art previous to the present work.

In a second series of experiments, the association of amiodarone and beta-blocker was investigated. To find out whether the action of amiodarone is uniquely due to its effect on beta adrenergic receptors, and to study dose ranges at which synergy occurs and the limits of contraindications, progressively increasing doses of amiodarone and a beta-blocker were administered to patients suffering from a stable chronic angina in the two orders: The following surprising observations were made:

When the beta-blocker was administered first, followed by amiodarone there was a statistically higher efficacy with the combination of drugs in comparison to the beta-blocker only, with no significant major undesirable effect in a group of 81 patients.

The experiment was performed as follows: A beta-blocker was administered over a period of 3 weeks followed by the administration of the beta-blocker to half of the patients and a reduced dose of beta-blocker in combination with amiodarone to the other half for a second period of 6 weeks with measurements of relevant parameters at 3 weeks interval. A superiority of the association of drugs was observed on the statistical analysis of the symptoms and of electrical parameters on exercise electrocardiography in the patients as a whole as well as on 24 hours dynamic E.C.G. monitoring in 12 patients. This suggests the presence of a pharmacological action that is clinically and statistically significant and that is distinct from an anti-adrenergic action. The beta-blocker used was atenolol in 35 cases, acebutolol in 10 cases, metoprolol in 10 cases, sotalol in 10 cases, tertatolol in 6 cases and propanolol in 10 cases.

When amiodarone was administered first followed by a beta-blocker in 30 cases, significant additional effects on heart rate, blood pressure and sometimes mild increases in auriculo-ventricular conductions were observed after administration of lesser doses than usual of the beta-blocker. These increments of observed effects occurred rapidly with the first doses of the beta-blocker. Exercise duration on bicycle tests increased sharply and significantly when exercise was limited previously by angina and ST segment change. The increase in exercise capacity was associated with a greater intensity of the detectable anti-ischemic effect of the combination. These were observed with atenolol, acebutolol and propanolol. Thus the association of amiodarone with a beta-blocker, with the advice that the patient receives the beta-blocker first and that it is checked that the patient can tolerate the beta-blocker at the cardiac level and that the auriculo-ventricular conduction is not abnormally increased, is a clinically useful observation. It thus appears that certain undesirable effects of the association of amiodarone and a beta-blocker are due to an increase of beta-blocking effects among certain patients who cannot tolerate a high beta-blocking effects. Testing with a beta-blocker when it shows no abnormal sensitivity to a beta-blocker allows the use of an association of a beta-blocker and amiodarone in the doses defined by the applicant.

The increase in conduction time when observed with the first doses of beta-blocker did not further increase with time with maintenance doses of both drugs. It is concluded that the highly beneficial effects of the proposed association are generally linked both to a mode of action specific to amiodarone and different from the beta-blocking effect and also to the obtention of a higher beta-blocking effect with a smaller than usual dose of beta-blocker. This facilitates the reduction of the dose of the beta-blocker on one hand and the reduction of the dose of amiodarone on the other hand. It also limits any secondary effects of both amiodarone and of a beta-blocker. Thus the combination of amiodarone and of a beta-blocker improves the quality of life of a patient with coronary insufficiency in comparison to the use of a beta-blocker only. Two main factors influence the global effect on the quality of life in anginal patients: exercise performance and sexual dysfunction. These two parameters are statistically much less severely affected by the combination of drugs at the doses used than with a beta-blocker alone at the standard dose (P<0,001) in a Quality of Life study performed simultaneously with the clinical study described above.

The association of amiodarone and beta-blocker by IV administration was studied. These studies were designed to compare in groups of 6 patients the effects of progressively increasing bolus doses of amiodarone and of propanolol, a beta-blocker with an immediate clinical effect. These were compared with effects of a propanolol-amiodarone combination containing progressively increasing doses of propanolol.

It was found 1) that administration of small doses of propanolol (1–5 mg) very significantly increased the clinical effects of small bolus of amiodarone 2) that the immediate effects of a rapid injection of an association of 1 mg of propanolol and 25 mg of amiodarone exceeded the immediate effects of those of 50 mg of amiodarone and exceeded the delayed effects of 4 mg of propanolol.

Based on these experiments a preparation was developed containing 1 mg of propanolol and 25 mg of amiodarone which was found to be at least as potent as 50 mg of amiodarone on certain parameters and as potent as 3 mg of propanolol on the same parameters and associated with less side-effects than the 2 drugs used separately in clinically potent doses.

The above-referenced doses of beta-blockers that potentiate I.V. amiodarone were found in studies of 2 groups of 8 patients with unstable angina to be synergistic with amiodarone in its anti-ischemic effects producing a much earlier effect on some parameters of ischemia (myocardial oxygen consumption and ST segment change) than when amiodarone is used alone. The dose of amiodarone required to produce in two hours, a 20% decrease in ST segment elevation is markedly reduced if 1 mg. of propanolol or 2 mg. of atenolol is concurrently administered.

In a third series of experiments, oral administration of the pharmaceutical preparations hereof were investigated in infarction and in the infarctoid syndrome.

A comparison was carried out in patients suffering from an infarction and examined within 30–60 minutes after the onset of pain the effects of the administration of a preparation administered by oral means: (i) Amiodarone 400 milligrams and (ii) Atenolol 50 milligrams.

More highly beneficial effects as measured by electrical indices of ischaemia and the usual indices of the consumption of oxygen were observed which did not induce any significant undesirable side effects.

The immediately foregoing experiments were repeated but substituting 100 mg acebutolol and 20 mg of propanolol respectively for 50 mg of atenolol. Once again, significantly beneficial effects were observed.

It thus appears that the beneficial effects observed in the two clinical conditions (chronic angina and acute infarctoid syndromes) by the administration of the association of amiodarone and atenolol, of amiodarone and acebutolol, of amiodarone and propanolol demonstrates a synergy of the effects of amiodarone on one hand and the effects of the beta-blocker on the other.

The beneficial effects of the association of amiodarone with acebutolol, of amiodarone with atenolol and of amiodarone with propanolol may be extended to the general class of beta-blockers.

MODES OF ADMINISTRATION AND CLINICAL USES a) Oral chronic administration

One treatment should ideally use the 2 active substances in the novel combination in a form for oral administration in weight ratios (approximate weight) of amiodarone/atenolol of 2:1 to 1:1 more particularly preferred in the ratio 50 mg:50 mg.

In presence of an acute sensitivity to the effects of beta-blockers and mainly among patients where the initial heart rate is low one can envisage a lower dose of beta-blocker for example: 25 mg atenolol instead of 50 mg and with a weight ratio of amiodarone/atenolol 2:1.

Where propranolol is used in place of Atenolol, the respective weights of this beta blovker would be 20 mg and 10 mg.

A tablet may be made of for example, amiodarone, and beta blocker using as excipients: lactose, maize, starch, povidone excipient, magnesium stearate, mannitol, sodium carboxy methyl cellulose, sodium carboxy methyl starch, colloidal silica.

c) Intravenous administration

The intravenous mode of administration is the preferred form of administration of the novel combinations during severe coronary insufficiency particularly in the setting of an infarction as it is the form most suitably adapted for the patient's conditions; it can be modulated with regards to the clinical evolution and the individual's susceptibility. This mode comprises the simultaneous administration of two or three compounds and the most preferred combination is that which allows the administration of three of the compounds.

The amiodarone:beta blocker ratio varies from 100:1 to 26:4 for propanolol from 100:1 to 50:10 for atenolol, from 50:2 to 26:10 for acebutolol and from 50:2 to 25:15 for metoprolol.

During the first hours of acute coronary insufficiency parenteral administration of 1–10 mg/kg of amiodarone and a hourly dose of 0.5–5 mg/hr of, say, propranolol are desirable. A 12 hour treatment period is suitable. The amount of amiodarone and propranolol required for optimal limitation and eventual prevention of an infarct is an average of 700 mg and 1.0 mg respectively administered in 24 hours for a 70 kg patient. The doses should then be adapted to clinical evolution particularly in ratios with respect to weight (approximate to exact) of amiodarone/propranolo varying from 100:1 to 10:1 preferentially 25:1 and in a way particularly preferred that contains 400 mg; 5 mg to be administered within 24 hours.

The bolus doses best adapted to the setting of an acute coronary emergency comprise, in the light of experiments performed the 2 substances in the ideal ratios of 25:1 to 25:2 and in the most preferred ratio of 25:2. The necessary dose is lower in patients with a normal arterial pressure, than in those with an elevated arterial pressure. Likewise, the effective and necessary doses are less important in cases of inferior infarction than in those with an anterior infarction, in elderly patients than in young patients.

Moreover in the presence of an acute coronary insufficiency and to prevent the occurrence of a myocardial infarction and to obtain an optimal limitation of infarct size and to prevent reperfusion arrythmias, it is discovered that a prolonged administration is desirable. Depending on the intensity of the infarctoid syndrome or of the unstable angina it is discovered that IV administration may optimally be prolonged to 12 hours using the average doses of 800 mg Amiodarona and 5 mg propanolol or to 24 hours using a total dose of 700 mg and 10 mg respectively in repeated bolus doses or slow I.V infusions. Some of the drugs may eventually be administered partly orally. In case of associated and simultaneous intravenous and oral administrations, the dose of the I.V. drugs may be decreased in consequence. One example of simultaneous I.V and oral dosage in emergency is as follows:

25 mg Amiodarone, 0.25 mg Propanolol I.V.
100 mg Amiodarone and 1 mg Propanolol I.V. (slow injection over 5 minutes).
400 mg Amiodarone orally The preferred ratio of amiodarone to beta-blocker in I.V. presentation is 25:1 in case of propanolol or 25:2 in case of atenolol.

The ideal forms of the apparatus for administration of the novel combinations for acute emergencies consist therefore of (1) either a syringe comprising 2 compartments containing the 2 active substances ready for use or (2) a kit containing two or three syringes ready to be fixed to a regulator with 3–4 tracks whereby one is fixed to a needle ready for use and the others to syringes containing the active substances already dosed according to the ratio amiodarons/beta blocker varying from 100:1 to 10:1 for immediate initial injection during the first minutes of medical intervention, and in a ratio of approximately 100 mg: 2 mg, for repeated injections during the early hours of infarction syndromes.

The combination may comprise a beta-blocker other than atenolol, acebutolol, satolol and metoprolol, such as tertatolol pindolol and labatolol.

The preferred approximate dose of IV beta-blocker to replace 1 mg of Atenolol is propanolol 1 mg, metoprolol 8 mg (slow injection), or acebutolol 5 mg.

The preferred dose of beta-blocker that may replace 50 mg atenolol in the combination is as follows: acebutolol approximately 100 mg of immediate release and 250 mg of slow release preparation 50 mg of metoprolol or tertatolol, approximately 2.5 mg.

The preferred achieved form of the invention in the treatment of extremely severe coronary insufficiency where human lives are at risk is that of liquid preparations suitable for parenteral administration.

EXAMPLES

EXAMPLE 1

I.V. Pharmaceutical Preparation

Presentation: Injectable solution in boxes of vials of 3 ml each.

Hospital or Mobile Coronary Care Unit Presentation: Boxes of 20 vials.

Preparation of solution so as to contain:

| | |
|---|---|
| amiodarone | 25 mg |
| propanolol | 1 mg |
| mannitol | 3 mg |
| glycine | 17.5 mg |
| sodium chloride | 30 mg |
| acetic acid | 0.12 mg |
| water/sodium hydroxide q.s | 3 ml at pH7 |

EXAMPLE II

Another I.V. Preparation

Presentation as in Ex. I in vials. Preparation of solution so as to contain:

| | |
|---|---|
| amiodarone | 25 mg |
| stenolol | 2 mg |
| mannitol | 3 mg |
| glycine | 17.5 mg |
| sodium chloride | 30 mg |
| acetic acid | 0.12 mg |
| water/sodium hydroxide q.s | 3 ml at pH7 |

EXAMPLE III

Tablet Composition

A tablet is made of the three following substances and proportions:

| | |
|---|---|
| amiodarone, | 75 mg; |
| stenolol, | 50 mg; |
| Other constituents: Excipients: | |
| lactose | 275 mg |
| maize starch | 80 mg |
| povidone excipient | 5 mg |
| magnesium stearate | 11 mg |
| colloidal silica | 2.5 mg |

EXAMPLE IV

A Capsule Containing Two or Three Compartments

I) A capsule is made of 2 compartments so as to comprise the following active substances and inactive ingredients, 1 compartment to comprise isosorbide mononitrate and its associated inactive ingredients for prolonged release.

| | Active Substances (approximate composition) | Inactive Ingredients (approximate composition) (in gm) | |
|---|---|---|---|
| 1. | Amiodarone chlorhydrate 0,075 g | Lactose | 0,025 |
| | | Maize starch | |
| | | Polyvidone excipient | 0,002 |
| | | Anhydrous colloidal silica | 0,0009 |
| | | Magnesium stearate | 0,0017 |
| | | Purified Water | 0,022 |
| 2. | Acebutoiol chlorhydrate 0,200 g | Lactose | 0,15 |
| | | Maize Starch | 0,45 |
| | | Polyvidone | 0,013 |
| | | Magnesium stearate | 0,004 |
| | | Talc | 0,001 |
| | | Aerosil 200 | 0,001 |

II) A capsule containing two compartments:
First compartment: amiodarone 100 mg
with inactive ingredients as in (I) above and
Second Compartment: acebutoiol (400 mg) in prolonged release form

EXAMPLE V

A Tablet for Both Sub-lingual and Oastro-Intestinal Administration

| | | | |
|---|---|---|---|
| amiodarone | | 50 mg | |
| metoproiol | | 50 mg | |
| Excipients: lactose | | 300 mg | |
| maize starch | 100 mg | magnesium stearate | 15 mg |
| colloidal silica | 2.5 mg | povidone excipient | 6 mg |

EXAMPLE VI

Preparation for oral Adminiatration in Emergency

| | |
|---|---|
| amiodarone | 400 mg |
| stenolol | 50 mg |

| Excipients: | |
|---|---|
| lactose | 300 mg |
| maize starch | 100 mg |
| povidone excipient | 6 mg |
| magnesium stearate | 15 mg |
| colloidal silica | 2.5 mg |

In Examples III through VI instead of atenolol, the combination may consist of another beta-blocker namely acebutolol, metoprolol, sotaiol, tertatolol and propanolol. A dose of 100 mg acebutolol of classical release pattern or 250 mg of slow release pattern may replace 50 mg atenolol in the preparation and a dose of 100 mg of metroprolol or 40 mg of sotaiol, or 2.5 mg of tertatolol or 20 mg of propanolol may also replace 50 mg of atenolol in the oral preparation.

EXAMPLE VII

Prepared Syringes and Kits and Methods of Treatment of Emergencies

Because of the necessity to adapt doses to individual cases and with the aim of preventing sudden deaths, a device is utilized that comprises in one unit:

(i) An already prepared syringe containing in one compartment a dose of 25 mg of amiodarone for bolus injection, in another compartment a dose of 100 mg of amiodarone for administration in a delay varying from 2 to 5 minutes after the first injection and a compartment containing 200 mg of amiodarone to be administered within a delay of 15 to 60 minutes after the second injection.

(ii) A compartment of a syringe containing 0.5 mg propranolol, another compartment containing 0.2 mg propranolol.

EXAMPLE VIII

Pre-filled Syringes Containing the Compositions Hereof

Mode (i) A prefilled multi-barrelled syringe containing in separate compartments for simultaneous administration:

| | |
|---|---|
| a) amiodarone | 25 mg, |
| benzyl alcohol | 15 mg |
| polysorbate 80 | 50 mg |
| water | 0.5 ml, |
| b) propanolol | 0,5 mg |
| citric acid | 20 mg |
| water | 1 ml, |
| Mode (II) A prefilled syringe containing in separate compartments | |
| a) amiodarone | 100 mg |
| benzyl alcohol | 60 mg |
| polysorbate 80 | 200 mg |
| water | 2 ml, |
| b) stenolol | 8 mg |
| citric acid | 20 mg |
| water | 1 ml. |

The syringe may be activated either manually or by a programmable micropump so as to eject individually adjusted doses of the preparation.

EXAMPLE IX

Alternative Dosage Equivalents

It will be understood by those skilled in the art that the different nitrates and beta blockers utilized in the present invention have different strengths per unit weight. Thus for a given range of dosage amount of amiodarone the equivalents of the other coagents which may be utilized in the compositions and methods of the present invention are set forth below:

| Nitrate | Oral Dose | Bolus | Maintenance |
|---|---|---|---|
| Beta Blockers | | | |
| Propanoiol | 20–80 mg | 1–5 mg | |
| Sotaiol | 40–80 mg | 2–40 mg | |
| Acebutoiol | 100–500 mg | 5–25 mg | |
| Atenoiol | 25–100 mg | 1–5 mg | |
| Metoproiol | 25–100 mg | 1–5 mg | |
| Pindoiol | 5–10 mg | | |
| Tertaiol | 2.5–5 mg | | |
| Amiodarone | 50–400 mg | 25–100 mg | 0.5–20 mg/kg/day |

EXAMPLE X

A Method of Treatment of Chronic Coronary Insufficiency with a View to Improve the Quality of Life and to Prevent the Recurrence of Sudden Death The sensitivity to a beta-blocker should first be determined by a test dose of a beta-blocker for example atenolol 50 mg administered orally on the first day and atenolol 100 mg to be administered on the second day. The absence of any unusually intense bradycardia, hypotension or atrio-ventricular block after the beta-blocker allows the use the invented preparations containing the 2 active substances.

One of the preparations of the present invention e.g. Example III is administered twice daily for six to 10 days until an optimal decrease in heart rate is observed e.g. so as to achieve a resting heart rate between 60 and 70 and an exercise heart rate less than 100 per minute.

The dose is then adapted to the results obtained and will usually vary between ½ and 1 ½ tablet per day.

EXAMPLE XI

Examples of a method of treatment of the acute coronary insufficiency present in the myocardial syndrome and in unstable angina with a view to prevent the occurrence of a myocardial infarction, to limit its size and to prevent sudden deaths.

Oral administration of the preparation in Example VI by the patient prior to the arrival of the medical team and as soon as possible after onset of chest pain.

Administration by the physician or CPR team of the preparation of Example I intravenously. Repeated bolus injections to be administered by the medical team according to observed results on blood pressure, heart rate and other clinical symptoms and signs. This is followed by a continuous infusion of a preparation containing the 2 active substances, in association eventually with a nitrate or thrombolytic agent.

I claim:

1. A method of providing cardioprotective action to a patient suffering from coronary insufficiency and complications thereof which comprises administering to such patient a cardioprotectively sufficient amount of protective agents comprising amiodarone in conjunction with at least one beta blocker.

2. A method of claim 1 wherein the protective agents are administered separately by at least one of the routes of administration selected from the group of methods consisting essentially of oral, sublingual, intravenous, subcutaneous, and inhalation administrative routes.

3. A method of claim 1 wherein the protective agents are administered in associated form by at least one of the routes of administration selected from the group of methods consisting essentially of oral, sublingual, intravenous, subcutaneous, and inhalation administrative routes.

4. A method of claim 1 wherein the ratio by weight of amidarone to the beta blocker is 100 to between 8 and 25.

5. A method of claim 1 wherein the administered dosage is between about 0.3 and about 30 mg per kg bodyweight per day.

6. A method of claim 1 wherein the protective agents are administered within the first 30 minutes after onset of apparent cardiac insufficiency.

7. A method of claim 1 wherein the administration is repeated at least once at intervals of between 30 and 60 minutes after the first administration.

8. A method of claim 1 wherein the beta blocker is selected from the group consisting of acetbutolol, metoprolol and atenolol.

9. A cardioprotective agent for administration to a patient suffering from coronary insufficiency to thereby reduce the probability of incidence of myocardial infarction in such a patient which comprises a combination of cardioprotectively sufficient amounts of amiodarone, at least one beta blocker and a pharmacologically acceptable carrier.

10. An agent of claim 9 wherein the ratio by weight of amidarone to beta blocker is 100 to between 8 and 25.

11. An agent of claim 10 wherein the beta blocker is selected from the group consisting of propanolol, acebutolol, metoprolol and atenolol.

12. An agent of claim 10 wherein the components are compounded in a form suitable for administration by the oral, sublingual, intravenous, subcutaneous, or inhalation administrative routes.

* * * * *